United States Patent
Liao

(10) Patent No.: US 7,393,402 B2
(45) Date of Patent: Jul. 1, 2008

(54) PURE PEARL POWDER PREPARATION METHOD

(76) Inventor: Chin-Tang Liao, No. 369-20, Jhensing Rd., East District, Taichung City 401 (TW)

( * ) Notice: Subject to any disclaimer, the term of this patent is extended or adjusted under 35 U.S.C. 154(b) by 0 days.

(21) Appl. No.: 11/653,302

(22) Filed: Jan. 16, 2007

(65) Prior Publication Data

US 2007/0166393 A1    Jul. 19, 2007

(30) Foreign Application Priority Data

Jan. 17, 2006    (CN) .................... 2006 1 0032889

(51) Int. Cl.
*C04B 14/00* (2006.01)
(52) U.S. Cl. ...................................... 106/400
(58) Field of Classification Search .................. 106/415
See application file for complete search history.

(56) References Cited

U.S. PATENT DOCUMENTS

2005/0226830 A1*  10/2005  Fang ........................... 424/63

* cited by examiner

*Primary Examiner*—Jerry A. Lorengo
*Assistant Examiner*—Shuangyi Abu Ali
(74) *Attorney, Agent, or Firm*—Browdy & Neimark

(57) ABSTRACT

A pure pearl powder preparation method of preparing a pure pearl powder by: (a) preparing pearl and washing the prepared pearl to remove sands and other, and then infusing the washed pearl in milk/soybean milk till that the milk/soybean milk becomes rancid, (b) washing the pearl with water to remove foul smell from the pearl, and then drying the pearl, and crushing the pearl into a superfine pearl powder, and (c) mixing the superfine pearl powder thus obtained with water in a high-speed mixer to form a pearl powder suspension, and then drawing the pearl powder suspension out of the mixer through a sieve over 100 mesh, and then drying the collected pearl powder suspension at low temperature to obtain the desired pure pearl powder.

8 Claims, No Drawings

PURE PEARL POWDER PREPARATION METHOD

BACKGROUND OF THE INVENTION

1. Field of the Invention

The present invention relates generally to material processing and more particularly, to a method of preparing pure pearl powder.

2. Description of the Related Art

Pearl is a noble Chinese medicine. According to modern scientific searches, pearl contains various amino acids including Asp, Thr, Ser, Glu, Gly, Ala, Gys, Val, Met, Ile, Leu, Tyr, Ph., Lys, His, Arg, Pro, Taurine and etc. Pearl also contains many minor elements necessary for human body such as Fe, Zn, Cu, Co, Mn, Cr, Se, I, Ni, F, Mo, V, Sn, Sr, Ge, and etc. Pearl is effective in tranquilizing the mind, improving eyesight, detoxifying chemicals and promoting granulation. It is a good for anti-aging beauty and healthcare applications. However, pearl is a mixed organic-inorganic nanostructured material, comprising two layers of calcium carbonate of aragonite structure and a layer of protein of thickness ranging from several nanometers to ten and more nanometers sandwiched between the two layers of calcium carbonate. Therefore, pearl has the characteristics of high hardness and toughness. Processing of pearl is not easy. Conventionally, there are two ways to process pearl, i.e., the dry grinding method and water-adding grinding method. Pearl powder obtained by the method dry grinding has a relatively greater grain size about several tens of nanometers in diameter that is not effective for absorption in human body. Further, this pearl powder processing method cannot remove heavy metal and other impurities. The water-adding grinding method can remove impurities, however it is not suitable for industrial production because of the drawbacks of high consumption of energy and time during processing.

SUMMARY OF THE INVENTION

The present invention has been accomplished under the circumstances in view. It is the main object of the present invention to provide a pure pearl preparation method, which combines drying grinding and water-adding grinding, practical for industrial production.

The pure pearl preparation of the present invention is to wash prepared natural pearl with running water to remove sands and other impurities, and then to infuse the washed clean pearl in stale soybean milk or milk in the open air for a certain length of time for enabling rancid soybean milk or milk to corrode surface $CaCO^2$ of the pearl into a rough surface to increase its surface friction power, and then wash the corroded pearl with clean water to remove bad smell, and then dry the pearl, and then grind the dried pearl into fine pearl powder, and then put the fine pearl powder in a high-speed mixer and add water and then starting the mixing rod, thereby forming a pearl suspension. According to our tests, the pearl powder is not soluble in water. The specific gravity of pearl is about 2.68~2.7 g. Big grain size pearl powder will settle to the bottom of water rapidly. However, fine pearl power will form a suspension when mixed with water at a high speed, and will settle to the bottom gradually about 5 minutes after stop of the mixing action. Based on this principle, the invention uses a high-speed mixer over 1000 r.p.m. to mix fine pearl powder prepared according to the aforesaid procedure with water. When a pearl suspension, stop the mixing action, and then draw the pearl suspension out of the mixer through a 1000 mesh sieve, and then add water and repeat the aforesaid procedure, and then collect the pearl powder solution filtered through the 1000 mesh sieve and dry the pearl suspension at low temperatures so as to obtain the desired pure pearl powder. The pearl powder that does not pass through the 1000 mesh screen and the pearl powder sediment containing heavy metals that is settled to the bottom of the mixer are thrown away. Therefore, the pure pearl powder preparation method of the present invention greatly reduces the heavy metal content in pearl powder.

The pure pearl powder preparation method includes the steps of:

(1) wash pearl with running water and screen washed pearl with a screen to remove sands and stones and other solid matters;

(2) infuse the washed pearl in milk or in soybean milk prepared under the ratio of soybean:water at 1:10~1:50 for more than 72 hours in such a manner that the level of the milk covers all the pearl, and then pour out soybean milk or milk, and then wash the pearl with a big amount of water to remove foul smell from the pearl, and then dry the pearl by means of natural wind or heating;

(3) use a 300-mesh crushing machine to crush the dry pearl thus obtained into a superfine pearl powder;

(4) put the fine pearl powder thus obtained in a mixer and add more than 10 times of water, and then start the mixer to mix the fine pearl powder with the water at 1000 r.p.m. for more than 10 minutes, and then stop the mixer;

(5) draw the suspension out of the mixer through a 1000 mesh sieve, and then add water to the mixer and repeat the aforesaid procedure; and (6) collect all the pearl powder suspension that passed the 1000 mesh sieve and dry it at low temperature so as to obtain pure pearl powder of grain diameter below 1 nanometer.

DETAILED DESCRIPTION OF THE INVENTION

Example 1

Pearl Powder Preparation Method I (1) 10 kg pearl was prepared, the pearl was washed with clean water and screened to remove sands and stones and other solid matters;

(2) the washed pearl was infused in stale soybean milk prepared under the ratio of soybean:water at 1:10 for more than 72 hours in such a manner that the level of the milk covered all the pearl, and then stale soybean milk was poured out, and then the pearl was washed with a big amount of water to remove foul smell from the pearl, and then the pearl was dried by heating;

(3) a 300-mesh crushing machine wash operated to crush the dry pearl thus obtained into a superfine pearl powder;

(4) the fine pearl powder thus obtained was put in a mixer and more than 10 times of water was added, and then the mixer was started to mix the fine pearl powder with the water at 1000 r.p.m. for more than 10 minutes, and then the mixer was stopped;

(5) the suspension was drawn out of the mixer through a 1000 mesh sieve, and then water was added to the mixer and the aforesaid procedure was repeated;

(6) all pearl powder suspension that passed the 1000 mesh sieve was collected and dried at 18° C. into a pure pearl powder, the pure pearl powder was weighted to be 6 kg, i.e., harvesting rate: 60%;

(7) the grain diameter of the pure pearl powder thus obtained was measured to be at 50~100 nm.

The heavy metal contents of the pure pearl powder thus obtained shows the contents of arsenic, lead, and mercury to be 2.28 ppm, 0.36 ppm, and 0.62 ppm respectively: When directly crush untreated pearl with a 300-mesh crushing machine into pearl powder, the contents of arsenic, lead, and mercury of the pearl powder to be 5.26 ppm, 117.63 ppm, and 3.89 ppm respectively:

Example 1I

Pearl Powder Preparation Method II (1) 10 kg pearl was prepared, the pearl was washed with clean water and screened to remove sands and stones and other solid matters;

(2) the washed pearl was infused in stale soybean milk prepared under the ratio of soybean:water at 1:20 for more than 72 hours in such a manner that the level of the milk covered all the pearl, and then stale soybean milk was poured out, and then the pearl was washed with a big amount of water to remove foul smell from the pearl, and then the pearl was dried by heating;

(3) a 350-mesh crushing machine wash operated to crush the dry pearl thus obtained into a superfine pearl powder;

(4) the fine pearl powder thus obtained was put in a mixer and more than 10 times of water was added, and then the mixer was started to mix the fine pearl powder with the water at 1500 r.p.m. for more than 15 minutes, and then the mixer was stopped;

(5) the suspension was drawn out of the mixer through a 2000 mesh sieve, and then water was added to the mixer and the aforesaid procedure was repeated;

(6) all pearl powder suspension that passed the 2000 mesh sieve was collected and dried at 18° C. into a pure pearl powder, the pure pearl powder was weighted to be 5 kg, i.e., harvesting rate: 50%;

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A pure pearl powder preparation method comprising the steps of:
   (a) preparing pearl and washing the prepared pearl to remove sands and other solid material, and then infusing the washed pearl into stale soybean milk or stale milk;
   (b) washing the pearl with water to remove foul smell from the pearl, and then drying the pearl, and crushing the pearl into a pearl powder by a crushing machine over 300 mesh; and
   (c) mixing the pearl powder thus obtained with water in a mixer to form a pearl powder suspension, and then drawing the pearl powder suspension out of the mixer through a sieve over 100 mesh, and then drying the pearl powder suspension to obtain the pure pearl powder, wherein the mixer is operated at least 1000 r.p.m, during step (c).

2. The pure pearl powder preparation method as claimed in claim 1, wherein the washed pearl is infused in stale soybean milk or stale milk for more than 72 hours during step (a).

3. The pure pearl powder preparation method as claimed in claim 1, wherein the pearl powder is mixed with more than 10 times of water in the mixer during step (c).

4. The pure pearl powder preparation method as claimed in claim 1, wherein the pearl powder is mixed with water in the mixer at a mixing time over 10 minutes during step (c).

5. A pure pearl powder preparation method comprising:
   (a) preparing pearl and washing the prepared pearl to remove sand, and then infusing the washed pearl into stale soybean milk or stale milk;
   (b) washing the pearl with water to remove foul smell from the pearl, and then drying the pearl, and crushing the pearl into a pearl powder by a crushing machine, over 300 mesh; and
   (c) mixing the pearl powder thus obtained with water in a mixer to form a pearl powder suspension, and then drawing the pearl powder suspension out of the mixer through a sieve, and then drying the pearl powder suspension to obtain the pure pearl powder, wherein the sieve through which the pearl powder suspension is drawn out of the mixer is a 2000 mesh sieve.

6. The pure pearl powder preparation method as claimed in claim 5, wherein the mixer is operated at at least 1000 r.p.m. during step (c).

7. The pure pearl powder preparation method as claimed in claim 6, wherein the pearl powder is mixed with water in the mixer at a mixing time over 10 minutes during step (c).

8. The pure pearl powder preparation method as claimed in claim 1, wherein the pearl powder suspension is drawn out of the mixer through a 2000 mesh sieve.

* * * * *